(12) United States Patent
Hansen et al.

(10) Patent No.: US 10,758,211 B2
(45) Date of Patent: Sep. 1, 2020

(54) CONTAINER AND CAP FOR A BIOLOGICAL SPECIMEN

(71) Applicant: BECTON DICKINSON AND COMPANY, Franklin Lakes, NJ (US)

(72) Inventors: Timothy R. Hansen, Spring Grove, PA (US); Mark Talmer, Pepperell, MA (US); Kevin Bailey, Cockeysville, MD (US); Dwight Livingston, Fallston, MD (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 22 days.

(21) Appl. No.: 16/133,968

(22) Filed: Sep. 18, 2018

(65) Prior Publication Data

US 2019/0015083 A1 Jan. 17, 2019

Related U.S. Application Data

(60) Division of application No. 14/788,970, filed on Jul. 1, 2015, now Pat. No. 10,123,785, which is a (Continued)

(51) Int. Cl.
*A61B 10/00* (2006.01)
*G01N 33/487* (2006.01)
(Continued)

(52) U.S. Cl.
CPC .......... *A61B 10/0096* (2013.01); *B65D 25/04* (2013.01); *B65D 41/005* (2013.01); (Continued)

(58) Field of Classification Search
CPC ....... A61B 5/150251; B01L 2300/0618; B29B 2911/14346; B65D 1/04; B65D 25/04
See application file for complete search history.

(56) References Cited

U.S. PATENT DOCUMENTS

| 710,553 A | 10/1902 | Anderson |
| 3,394,861 A | 7/1968 | Truax |
| (Continued) | | |

FOREIGN PATENT DOCUMENTS

| DE | 2343987 B1 | 1/1975 |
| DE | 2637273 A1 | 2/1978 |
| (Continued) | | |

*Primary Examiner* — David A. Rogers
(74) *Attorney, Agent, or Firm* — Botos Churchill IP Law LLP

(57) ABSTRACT

A container for collecting a biological specimen is provided that includes a peripheral wall extending from a base. The container further includes a longitudinal tower disposed within the container. The tower forms a partition within the container to form at least a first chamber and a second chamber therein, wherein the first and second chambers are in fluid communication with one another. In addition, the container includes an insert disposed within the container opposite the base, the insert comprising at least a first opening and a second opening. The second opening provides access to the second chamber and is further configured to engage a specimen collecting device to leave a portion of the specimen collecting device within the second chamber. The first opening provides access to the first chamber and is further configured to receive a syringe therein for accessing the biological specimen. Associated systems and methods are also provided.

20 Claims, 13 Drawing Sheets

Related U.S. Application Data continuation of application No. 13/672,205, filed on Nov. 8, 2012, now Pat. No. 9,075,039.

(60) Provisional application No. 61/557,011, filed on Nov. 8, 2011.

(51) Int. Cl.
| | |
|---|---|
| *C12M 1/00* | (2006.01) |
| *B65D 25/04* | (2006.01) |
| *B65D 41/00* | (2006.01) |
| *A61J 1/14* | (2006.01) |
| *A61B 10/02* | (2006.01) |

(52) U.S. Cl.
CPC ....... *C12M 45/00* (2013.01); *G01N 33/48778* (2013.01); *A61B 2010/0074* (2013.01); *A61B 2010/0216* (2013.01); *A61J 1/1406* (2013.01); *A61J 1/1412* (2013.01); *A61J 1/1418* (2015.05)

(56) References Cited

U.S. PATENT DOCUMENTS

| | | |
|---|---|---|
| 3,545,932 A | 12/1970 | Gilford |
| 3,730,170 A | 5/1973 | Michael |
| 3,774,455 A | 11/1973 | Seidler et al. |
| 3,834,992 A | 9/1974 | Bohnke et al. |
| 3,859,671 A | 1/1975 | Tomasello |
| 4,040,791 A | 8/1977 | Kuntz |
| 4,065,536 A | 12/1977 | Lucas |
| 4,076,420 A | 2/1978 | De Maeyer et al. |
| 4,150,089 A | 4/1979 | Linet |
| 4,439,319 A | 3/1984 | Rock |
| 4,583,667 A | 4/1986 | Fishman et al. |
| 4,768,238 A | 9/1988 | Kleinberg et al. |
| 4,772,558 A | 9/1988 | Hammann |
| 4,813,433 A | 3/1989 | Downey |
| 4,859,610 A | 8/1989 | Maggio |
| 5,102,016 A | 4/1992 | Ball et al. |
| 5,155,019 A | 10/1992 | Sussman et al. |
| 5,232,108 A | 8/1993 | Nakamura |
| 5,242,066 A | 9/1993 | Kelsey |
| 5,287,733 A | 2/1994 | Oku et al. |
| 5,297,599 A | 3/1994 | Bucheli |
| 5,316,146 A | 5/1994 | Graff |
| 5,370,128 A | 12/1994 | Wainwright |
| 5,403,551 A | 4/1995 | Galloway et al. |
| 5,422,273 A * | 6/1995 | Garrison ............ A61B 10/0291 422/547 |
| 5,431,884 A | 7/1995 | McDonough et al. |
| 5,480,378 A | 1/1996 | Weis-Foh et al. |
| 5,482,170 A | 1/1996 | Semersky |
| 5,588,550 A | 12/1996 | Meyer |
| 5,638,828 A | 6/1997 | Lauks et al. |
| 5,849,241 A | 12/1998 | Connan |
| 5,871,611 A | 2/1999 | Valyi |
| 5,888,831 A | 3/1999 | Gautsch |
| 5,897,840 A | 4/1999 | Owens et al. |
| 5,945,070 A | 8/1999 | Kath et al. |
| 6,216,340 B1 | 4/2001 | Fassbind et al. |
| 6,277,646 B1 | 8/2001 | Guirguis et al. |
| 6,291,234 B1 | 9/2001 | Raz et al. |
| 6,346,087 B1 * | 2/2002 | Peltier ............ A61B 10/0096 600/569 |
| 6,390,324 B1 | 5/2002 | Everette et al. |
| 6,398,031 B1 | 6/2002 | Frezza |
| 6,554,602 B2 | 4/2003 | Deemer et al. |
| 6,562,299 B1 | 5/2003 | Ostgaard |
| 6,589,749 B1 | 7/2003 | Guirguis |
| 6,651,305 B2 | 11/2003 | Fassbind |
| 6,680,027 B2 | 1/2004 | Kang et al. |
| 6,984,119 B1 | 1/2006 | Hickman et al. |
| 7,097,057 B2 | 8/2006 | Classens |
| 7,163,115 B2 | 1/2007 | Whitley |
| 7,258,251 B2 | 8/2007 | Johnson |
| 7,296,703 B2 | 11/2007 | Lane |
| 7,316,805 B1 | 1/2008 | Viola et al. |
| 7,413,551 B2 | 8/2008 | Decker et al. |
| 7,470,404 B2 | 12/2008 | Kang et al. |
| 7,556,777 B2 | 7/2009 | Victor |
| 7,579,190 B2 | 8/2009 | Ostgaard |
| 7,648,680 B2 | 1/2010 | Anderson et al. |
| 7,666,357 B2 | 2/2010 | Sattler et al. |
| 7,666,359 B2 | 2/2010 | Sattler et al. |
| 7,674,434 B2 | 3/2010 | Sakal et al. |
| 7,795,036 B2 | 9/2010 | Johnson et al. |
| 7,799,560 B2 | 9/2010 | Wilson et al. |
| 7,807,476 B2 | 10/2010 | Pressman et al. |
| 7,823,745 B2 | 11/2010 | Esser et al. |
| 7,824,921 B1 | 11/2010 | Levy |
| 7,824,922 B2 | 11/2010 | Kacian et al. |
| 7,846,395 B2 | 12/2010 | Shaw |
| 7,871,568 B2 | 1/2011 | Liang |
| 7,887,758 B2 | 2/2011 | Ostagaard et al. |
| 8,156,786 B2 * | 4/2012 | Nowland ............ G01N 33/241 73/19.01 |
| 8,376,958 B2 * | 2/2013 | Larkin ............... A61B 10/0096 215/307 |
| 8,663,974 B2 | 3/2014 | Brown et al. |
| 8,956,855 B2 | 2/2015 | Cognard et al. |
| 9,199,780 B2 | 12/2015 | Azani |
| 9,282,951 B2 * | 3/2016 | Lonky .................... A61B 10/02 |
| 2002/0076825 A1 | 6/2002 | Cheng et al. |
| 2002/0107499 A1 | 8/2002 | Funk |
| 2003/0059347 A1 | 3/2003 | Ostgaard et al. |
| 2003/0109804 A1 | 6/2003 | Auerbach et al. |
| 2004/0091401 A1 | 5/2004 | Golabek et al. |
| 2004/0180427 A1 | 9/2004 | Chang |
| 2005/0070873 A1 | 3/2005 | Johnson |
| 2005/0234422 A1 | 10/2005 | Oh et al. |
| 2007/0073186 A1 * | 3/2007 | Decker ............... A61B 10/0045 600/569 |
| 2008/0077046 A1 * | 3/2008 | Burg .................. A61B 10/0291 600/569 |
| 2008/0286831 A1 | 11/2008 | Liang |
| 2009/0156962 A1 * | 6/2009 | Yong .................. A61B 10/0045 600/569 |
| 2009/0275859 A1 * | 11/2009 | Kim .................. A61B 10/0291 600/569 |
| 2010/0089925 A1 | 4/2010 | Peltier |
| 2010/0124780 A1 | 5/2010 | Larkin |
| 2010/0222196 A1 | 9/2010 | Ito et al. |
| 2010/0245803 A1 | 9/2010 | Samsoondar |
| 2010/0305472 A1 * | 12/2010 | Larkin ................ A61B 10/02 600/570 |
| 2010/0331522 A1 | 12/2010 | Irvine et al. |
| 2014/0370592 A1 | 12/2014 | Mitenyi et al. |
| 2017/0137201 A1 | 5/2017 | Jackson et al. |
| 2018/0072460 A1 | 3/2018 | Wolfson |

FOREIGN PATENT DOCUMENTS

| | | |
|---|---|---|
| EP | 0471570 A1 | 2/1992 |
| EP | 0675195 A1 | 10/1995 |
| EP | 0687635 A1 | 12/1995 |
| FR | 2071306 | 9/1971 |
| GB | 2207652 | 2/1989 |
| GB | 2404735 A | 2/2005 |
| WO | 2006125212 A2 | 11/2006 |
| WO | 2007073392 A1 | 6/2007 |
| WO | 2008030607 A2 | 3/2008 |
| WO | 2010131140 A1 | 11/2010 |

* cited by examiner

CONTAINER AND CAP FOR A BIOLOGICAL SPECIMEN

CROSS-REFERENCE TO RELATED APPLICATIONS

The present application is a divisional of U.S. patent application Ser. No. 14/788,970, filed Jul. 1, 2015, which is a continuation of U.S. patent application Ser. No. 13/672,205, filed on Nov. 8, 2012, which claims the benefit of the filing date of U.S. Provisional Patent Application No. 61/557,011, filed Nov. 8, 2011, the disclosures of which are hereby incorporated herein by reference.

BACKGROUND OF THE INVENTION

Embodiments of the present invention relate generally to a container, an assembly, a system, and a method for collecting a biological specimen, such as cytological samples.

Specimen containers, such as vials and associated caps, are routinely used for collecting biological specimens, such as cytological samples. For example, a biological specimen may be obtained from the cervix or vagina using a brush in conjunction with a pap smear test to screen for and detect cervical cancer, pre-cancerous lesions, atypical cells, and other cytological categories. The brush may then be placed in the vial so as to transfer the sample into the vial for subsequent processing and analysis (e.g., vortex mixing, aspiration, and slide analysis). In some instances, the brush is detachable and left in the vial.

Undesirable materials, however, such as mucous, may adhere to the brush when obtaining the sample, thereby being deposited in the vial, which can interfere with subsequent processing. As such, a need exists for an apparatus configured to minimize the interference from undesirable materials, such as mucous, that facilitates the collection and processing of a biological sample.

BRIEF SUMMARY OF THE INVENTION

Various embodiments of the present invention are directed to a container, an assembly, a system, and a method for collecting a biological specimen. In one embodiment, a container for collecting a biological specimen is provided. The container may include a peripheral wall extending from a base, wherein the peripheral wall and base define an interior surface and an exterior surface. The container may further include a longitudinal tower disposed within the container, wherein the tower forms a partition within the container to form at least a first chamber and a second chamber therein, wherein the first and second chambers are in fluid communication with one another. In some embodiments, the container may include an insert disposed within the container opposite the base, the insert comprising at least a first opening and a second opening defined therein, wherein the second opening is configured to provide access to the second chamber and is further configured to engage a specimen collecting device to thereby leave a portion of the specimen collecting device within the second chamber, and wherein the first opening is configured to provide access to the first chamber and is further configured to receive a syringe therein for accessing the biological specimen. In some embodiments, the container may further comprise a notch defined in the exterior surface and configured to position the apparatus in subsequent processing. The container may further include a tower disposed within the container such that the first chamber is located approximately radially opposite from the notch. In some embodiments, the tower may further comprise a base edge adjacent to the base and at least two longitudinal edges extending therefrom and to the insert, wherein the base edge and the at least two longitudinal edges do not contact the interior surface of the peripheral wall. According to some embodiments, the base may be sloped downwards towards the base edge of the tower.

According to some embodiments, the first and second chambers may be in fluid communication with one another along the entire length of the at least two longitudinal edges of the tower. In some embodiments, the insert may be integrally formed with the interior surface of the peripheral wall of the container. The top edge of the tower may be coupled to the insert. In some embodiments, the first chamber may have a volume smaller than the volume of the second chamber. In some embodiments, the peripheral wall may be cylindrical in shape. Further, the longitudinal tower may extend parallel to the longitudinal axis of the peripheral wall. In some embodiments, the first and second openings of the insert might not be in fluid communication with one another.

In some embodiments, a system for collecting a biological specimen is provided. The system may comprise a container for collecting a biological specimen comprising a peripheral wall extending from a base, wherein the peripheral wall and the base define an interior surface and an exterior surface. The system may further include a longitudinal tower disposed within the container, wherein the tower forms a partition within the container to form at least a first chamber and a second chamber therein, wherein the first and second chambers are in fluid communication with one another. In some embodiments, the system may include an insert disposed within the container opposite the base, the insert comprising at least a first opening and a second opening defined therein, wherein the second opening is configured to provide access to the second chamber and is further configured to engage a specimen collecting device to thereby leave a portion of the specimen collecting device within the second chamber, and wherein the first opening is configured to provide access to the first chamber and is further configured to receive a syringe therein for accessing the biological specimen. According to some embodiments, the system may further include a cap configured to cover the first and second openings and sealingly engage the peripheral wall, the cap including at least one engageable member configured to be engaged for securing and unsecuring the cap to the container.

In some embodiments, the system may include a specimen collecting device configured to obtain a biological specimen from a patient and transfer the biological specimen to the container. In addition, the specimen collecting device may include a container having a peripheral wall that further comprises a flange and a threaded exterior surface disposed opposite from the base. The container may include a notch defined by the exterior surface and configured to position the system in subsequent processing. According to some embodiments, the tower may further comprise a base edge adjacent to the base and at least two longitudinal edges extending therefrom and to the insert, wherein the base edge and at least the two longitudinal edges do not contact the interior surface of the peripheral wall. The base may be sloped downwards towards the base edge. In some embodiments, the first and second chambers may be in fluid communication with one another along the entire length of the at least two longitudinal edges.

According to some embodiments, the insert may be integrally formed with the interior surface of the peripheral wall of the container. The top edge of the tower may be coupled to the insert. In some embodiments, the longitudinal tower may extend parallel to a longitudinal axis of the peripheral wall. The system may further include an insert comprising a first and second opening defined therein, wherein the first and second openings are not in direct fluid communication with one another. In some embodiments, the cap including at least one engageable member configured to be engaged by a chuck for securing and unsecuring the cap to the container may include an engageable member comprising a plurality of fingers equally-spaced around and extending inwards from the circumference of the cap. The plurality of fingers may be configured to be engaged by a chuck for securing and unsecuring the cap to the container. According to some embodiments, the cap may comprise a central portion that is configured to be pierceable by a piercing instrument.

According to some embodiments, a method for collecting a biologic specimen is provided. The method may include obtaining a biological specimen with a biological specimen device. The method may further include inserting the biological specimen device into a container, the container comprising a peripheral wall extending from a base, wherein the peripheral wall and the base define an interior surface and an exterior surface. In some embodiments, the container may include a longitudinal tower disposed within the container, wherein the tower forms a partition within the container to form at least a first chamber and a second chamber therein, wherein the first and second chambers are in fluid communication with one another. According to some embodiments, the container may further include an insert disposed within the container opposite the base, wherein the insert comprises at least a first opening and a second opening defined therein, wherein the second opening is configured to provide access to the second chamber and is further configured to engage a specimen collecting device to thereby leave a portion of the specimen collecting device within the second chamber, and wherein the first opening is configured to provide access to the first chamber and is further configured to receive a syringe therein for accessing the biological specimen.

BRIEF DESCRIPTION OF THE DRAWINGS

Figure 1:
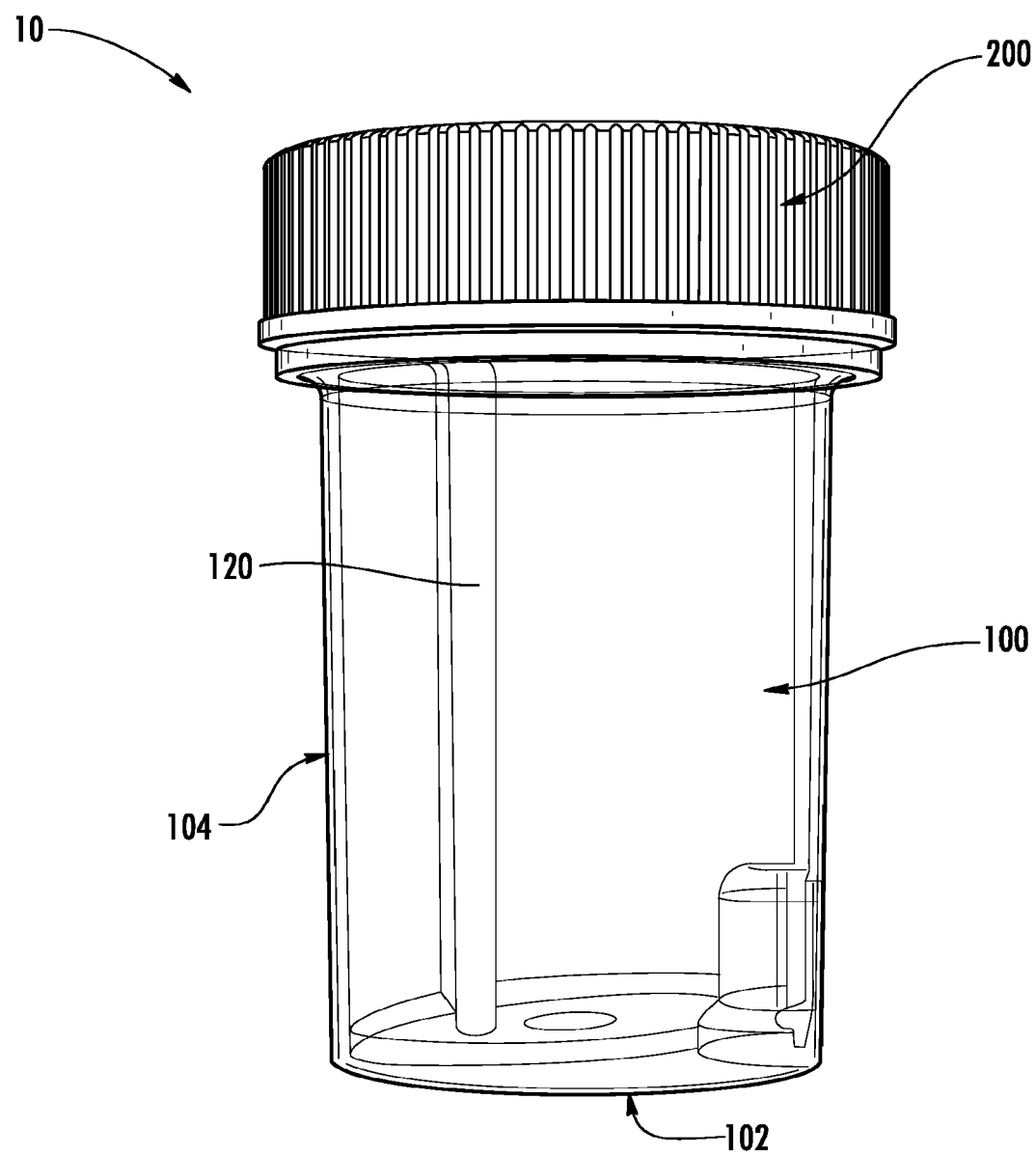
Figure 2:
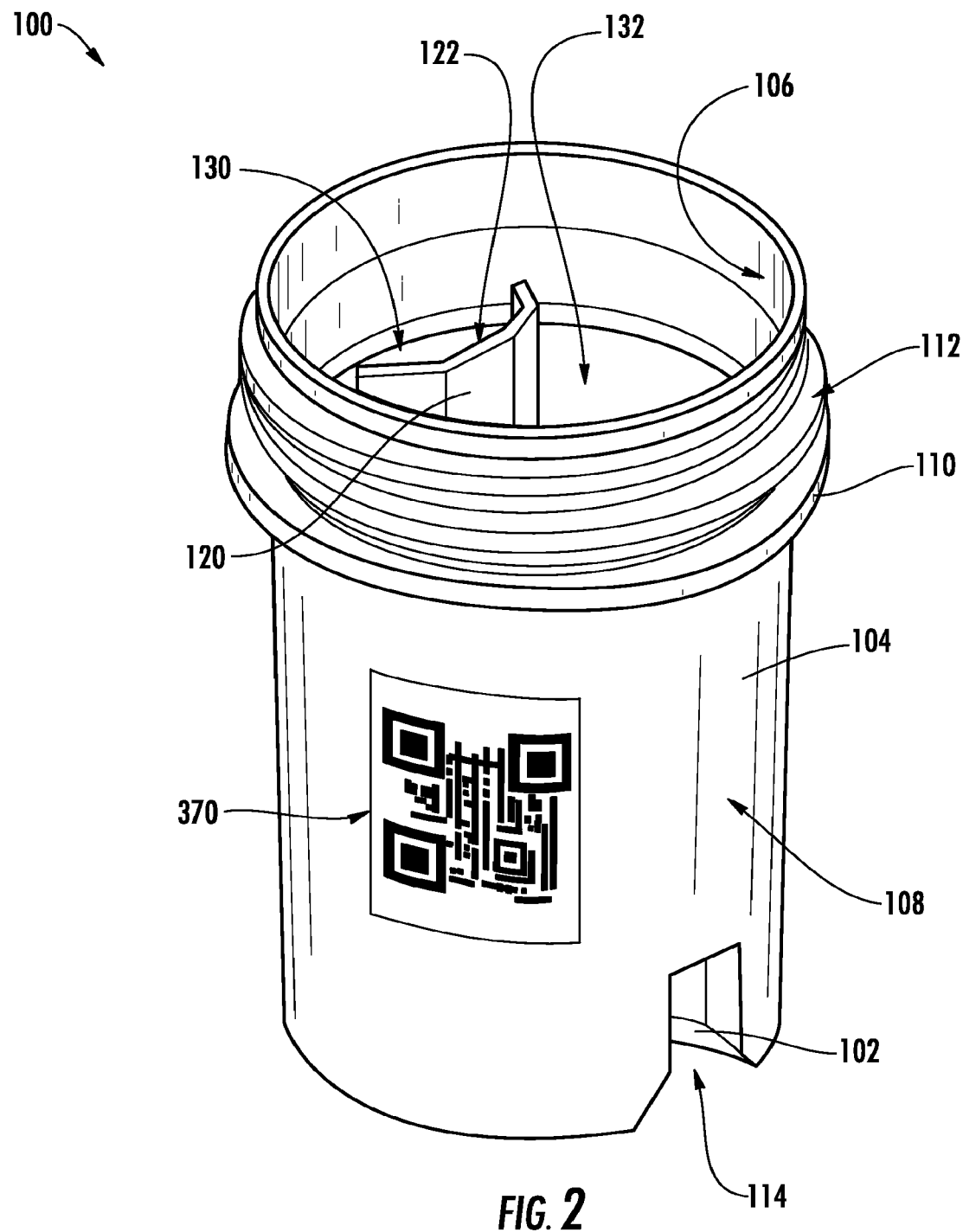
Figure 3:
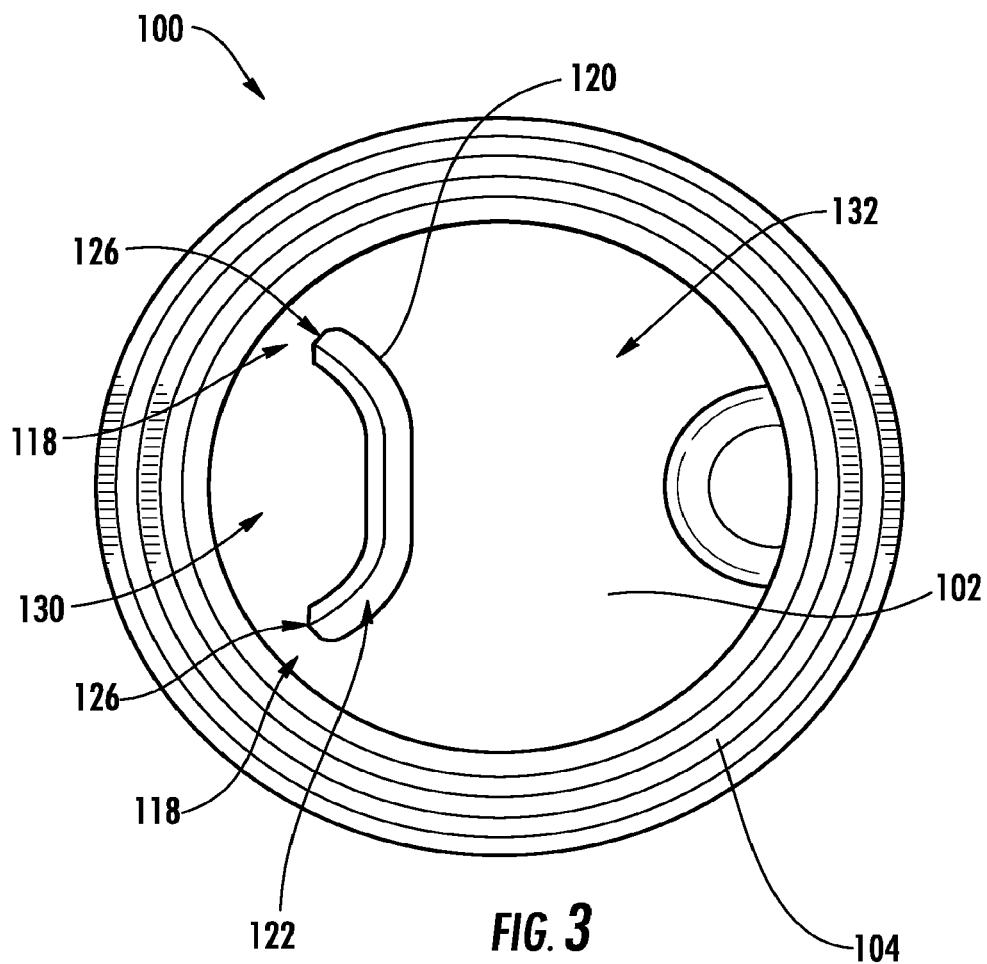
Figure 4:
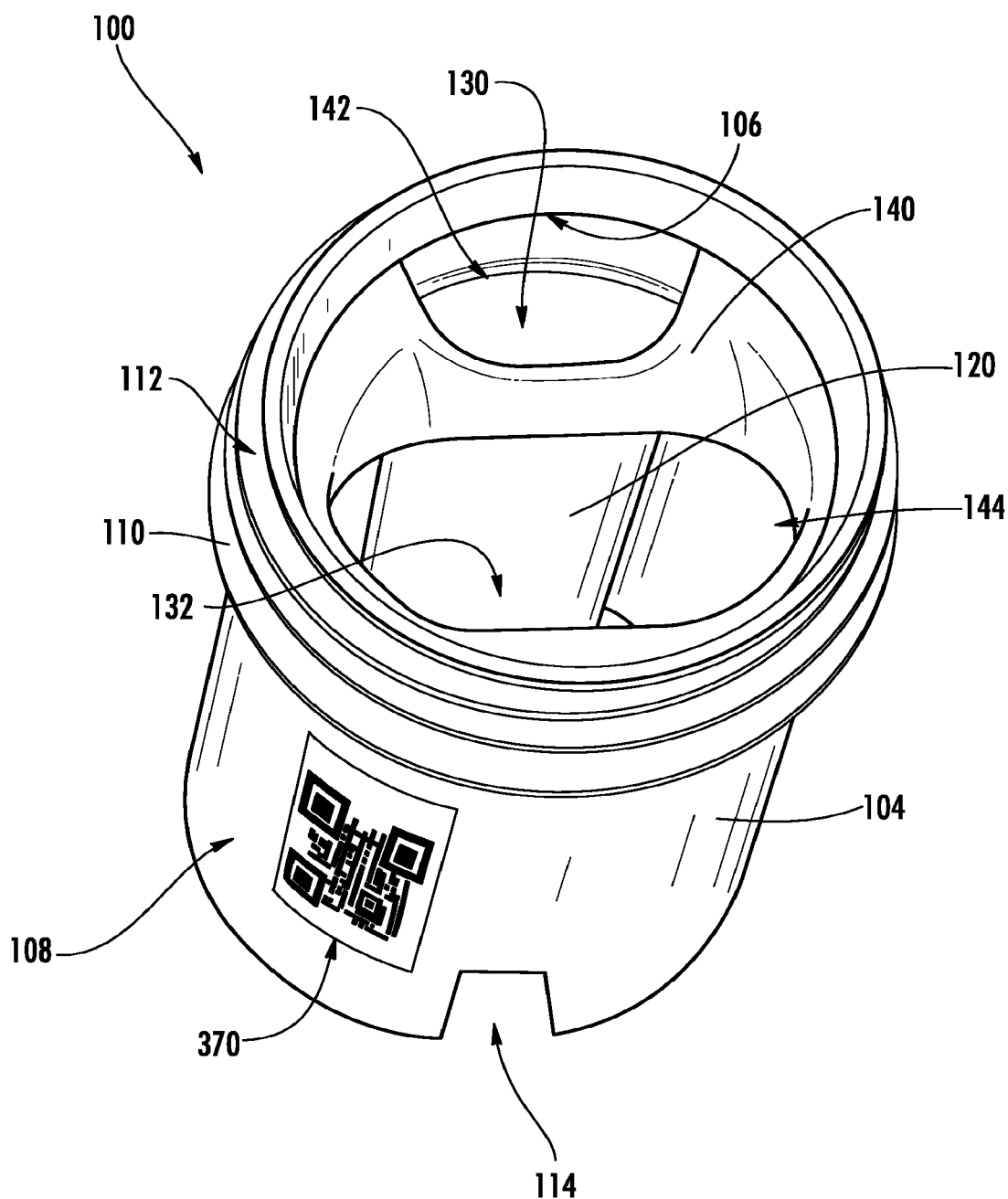
Figure 5:
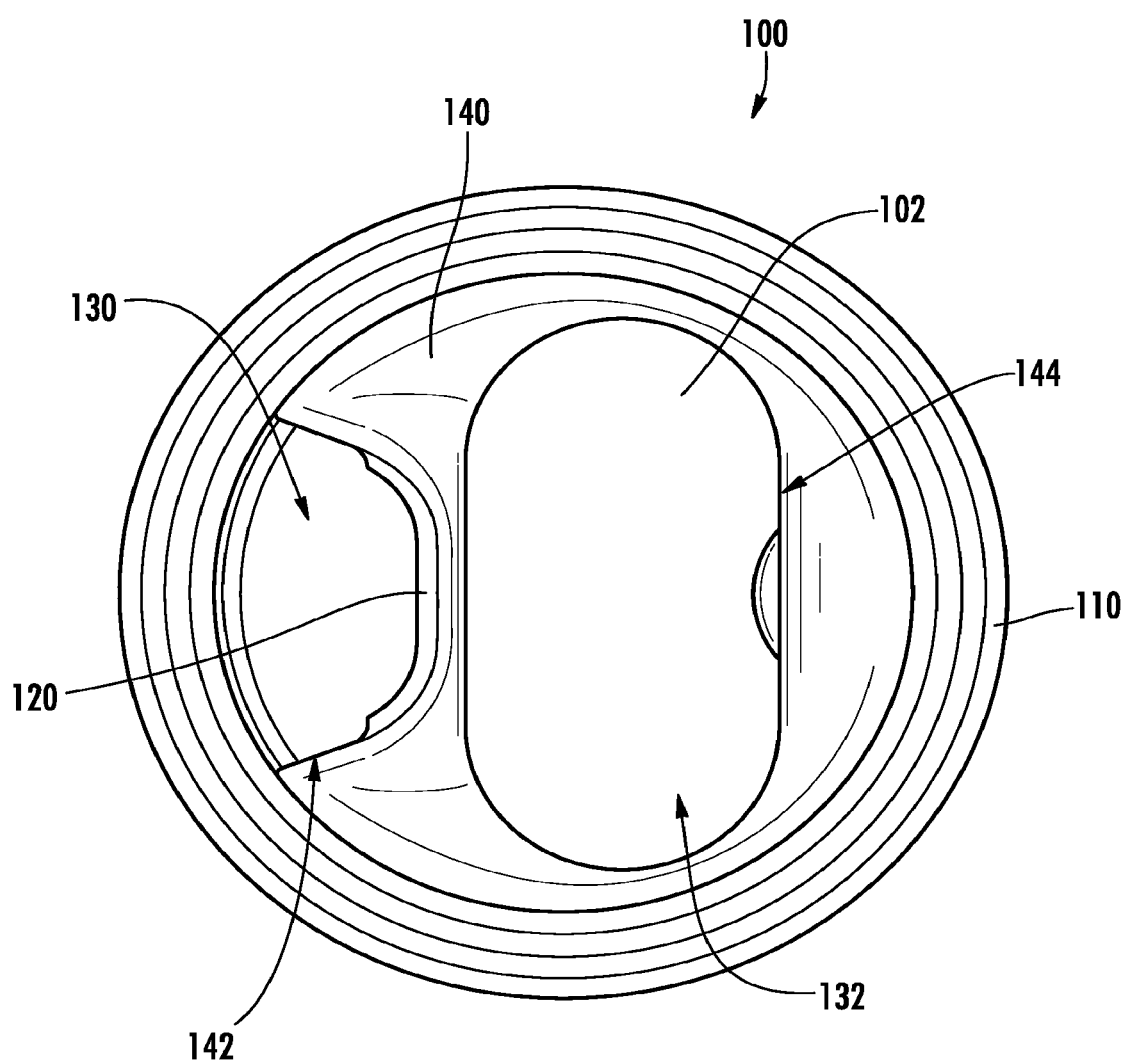
Figure 6A:
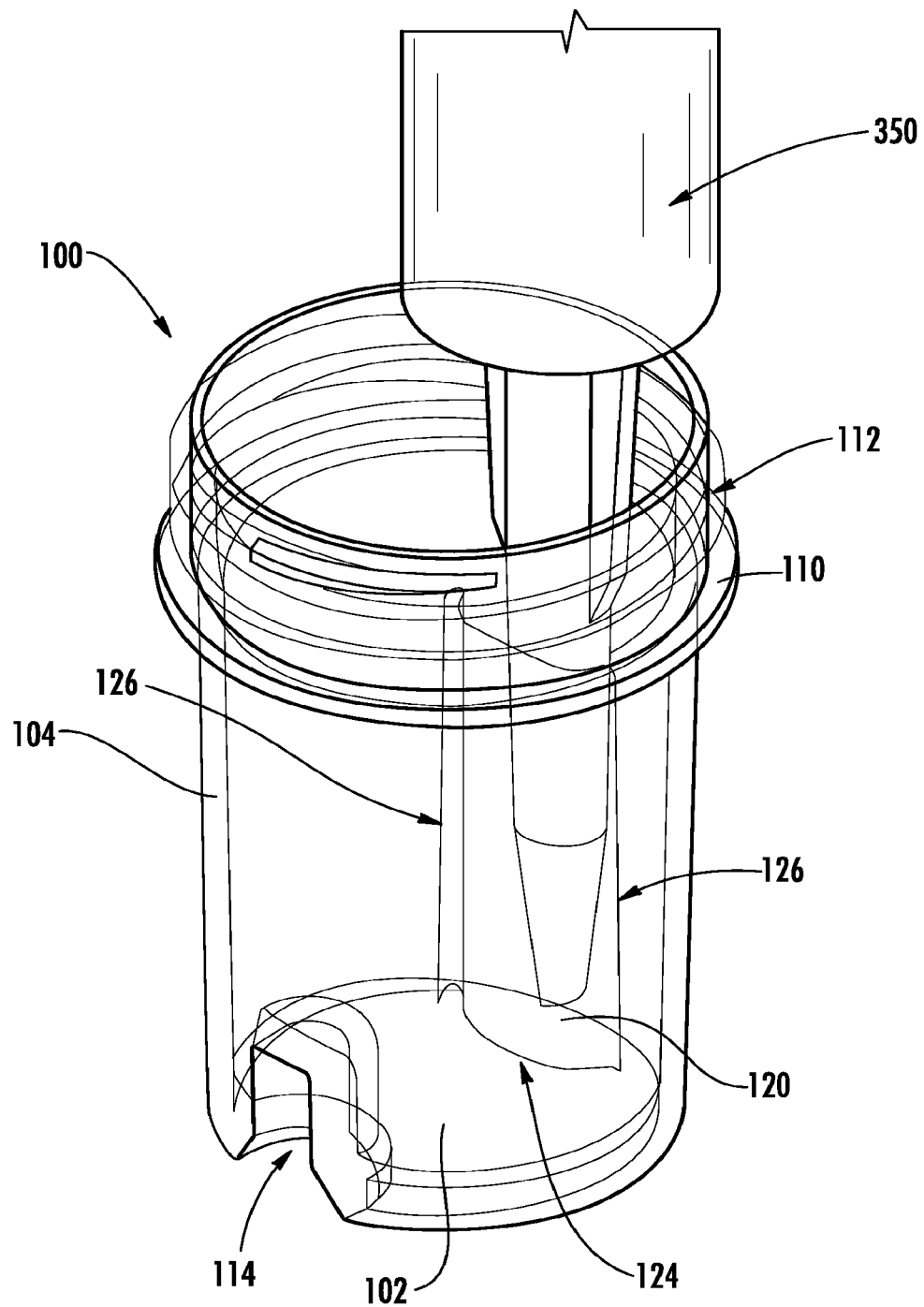
Figure 6B:
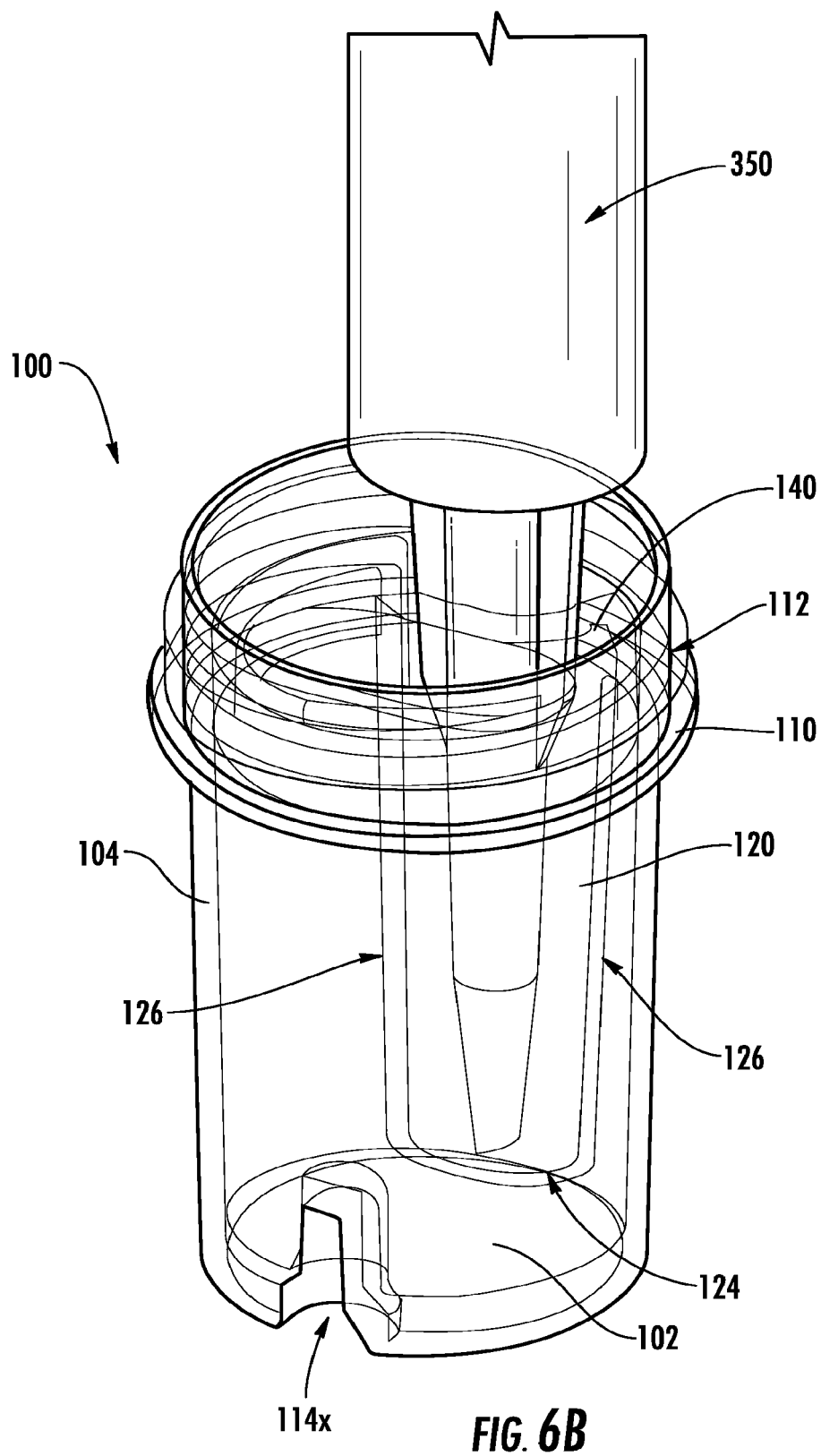
Figure 6C:
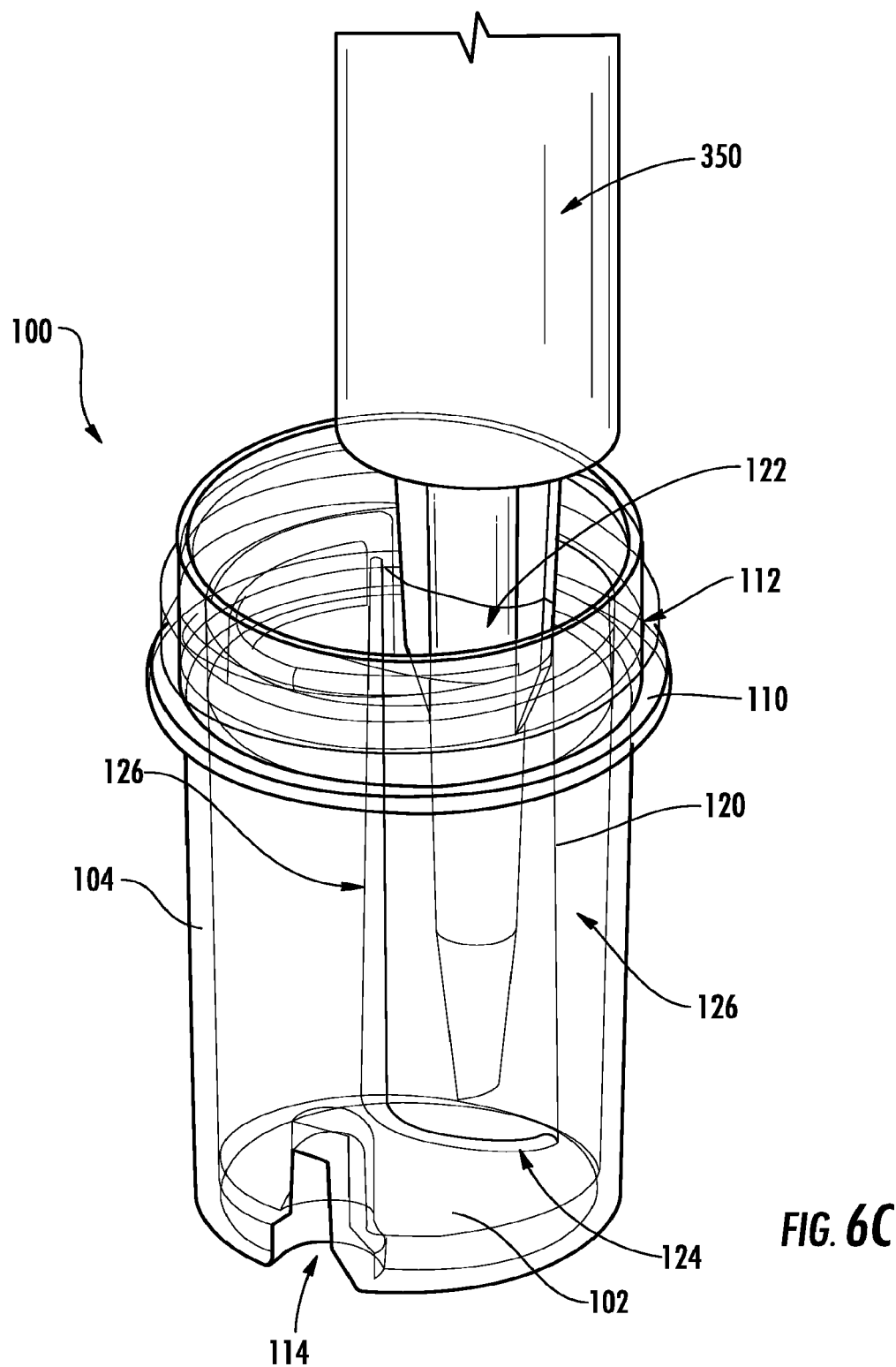
Figure 7:
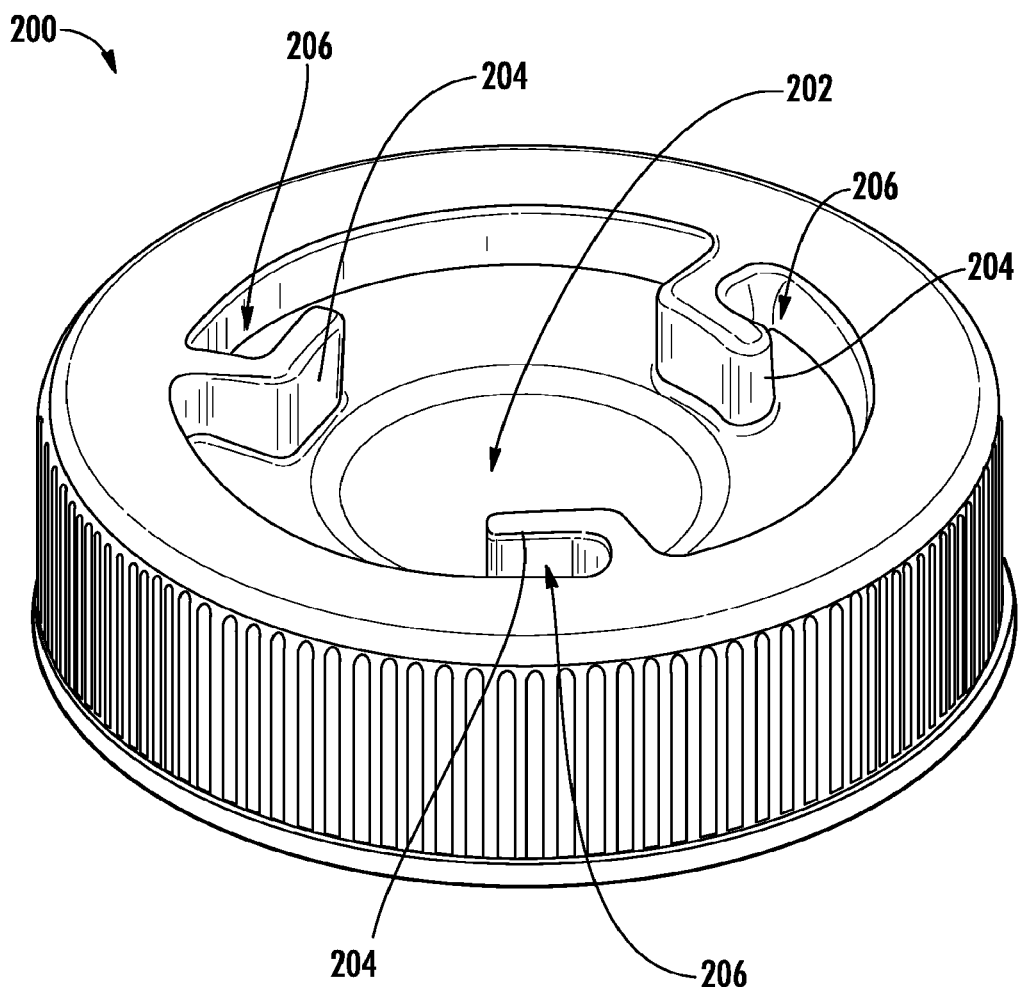
Figure 8:
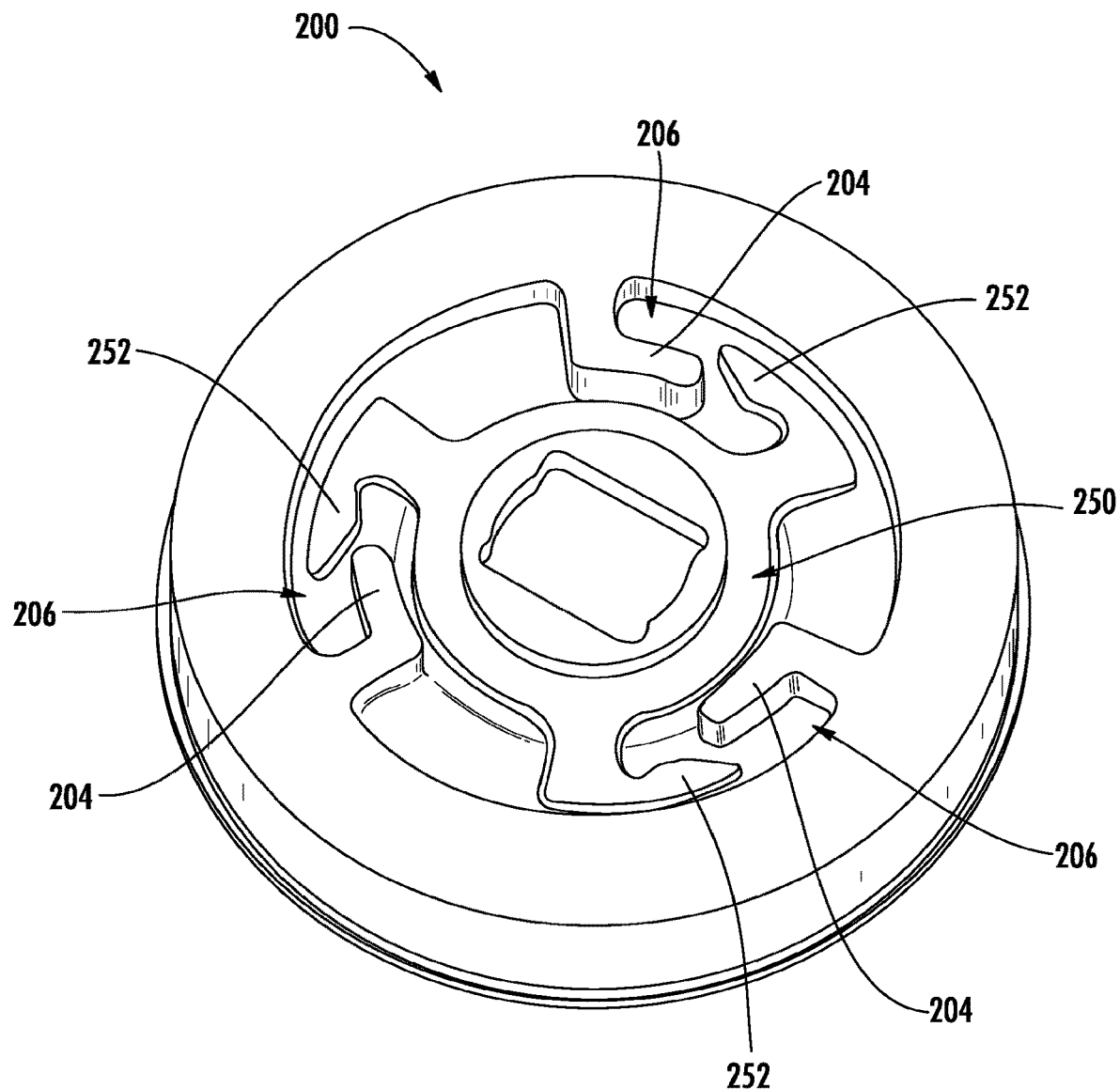
Figure 9:
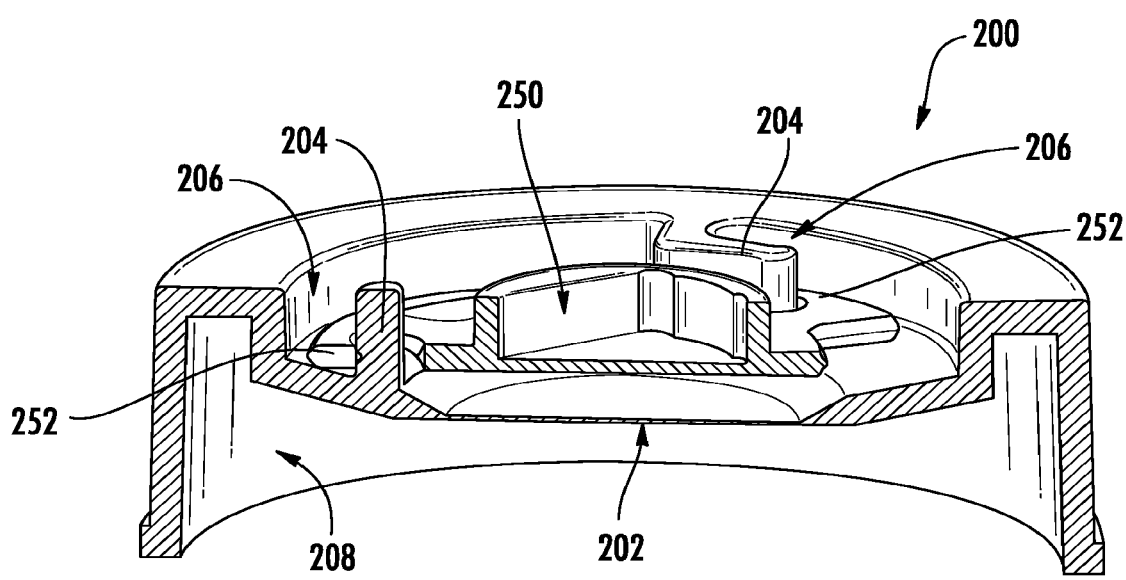
Figure 10:
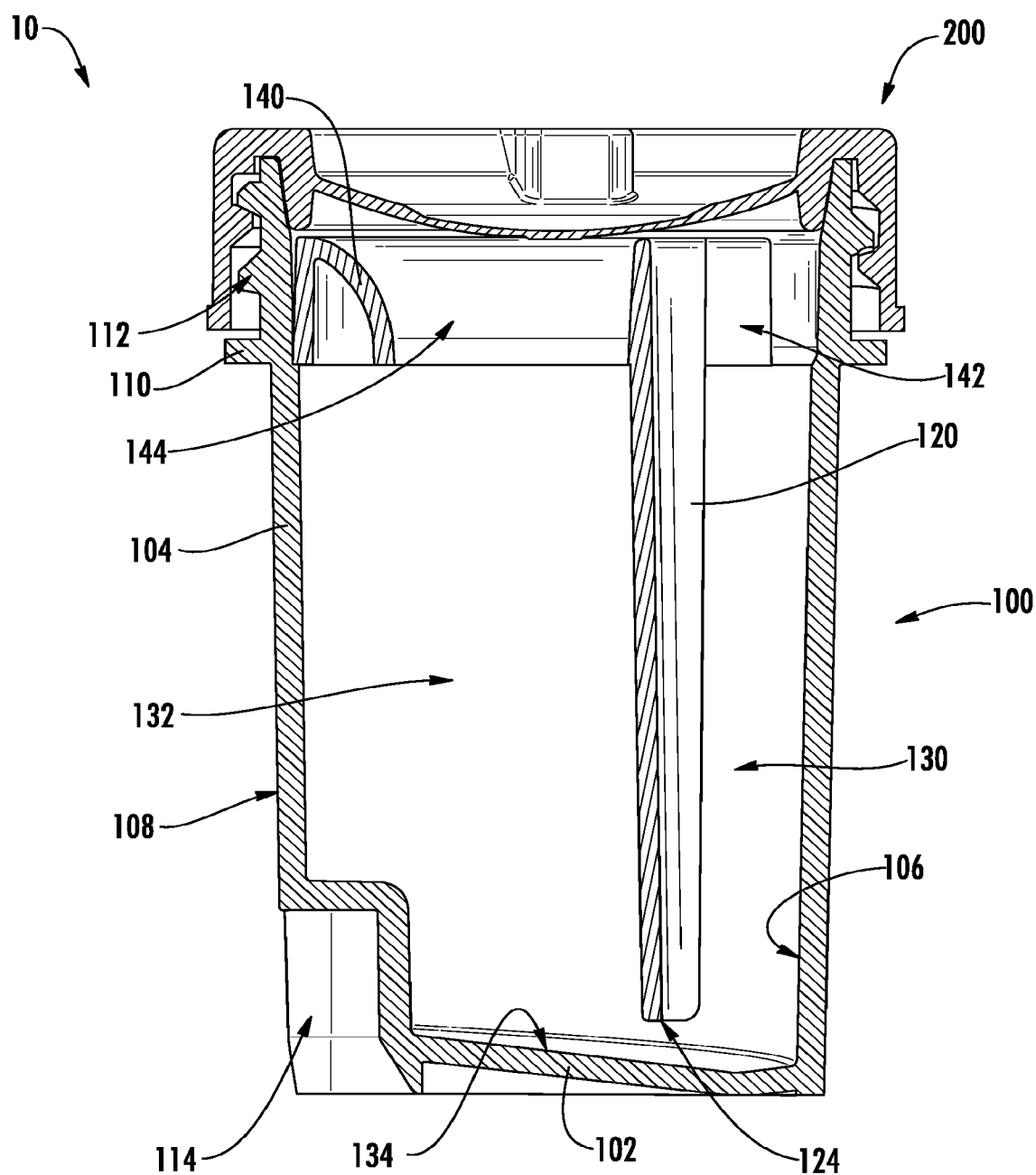
Figure 11:
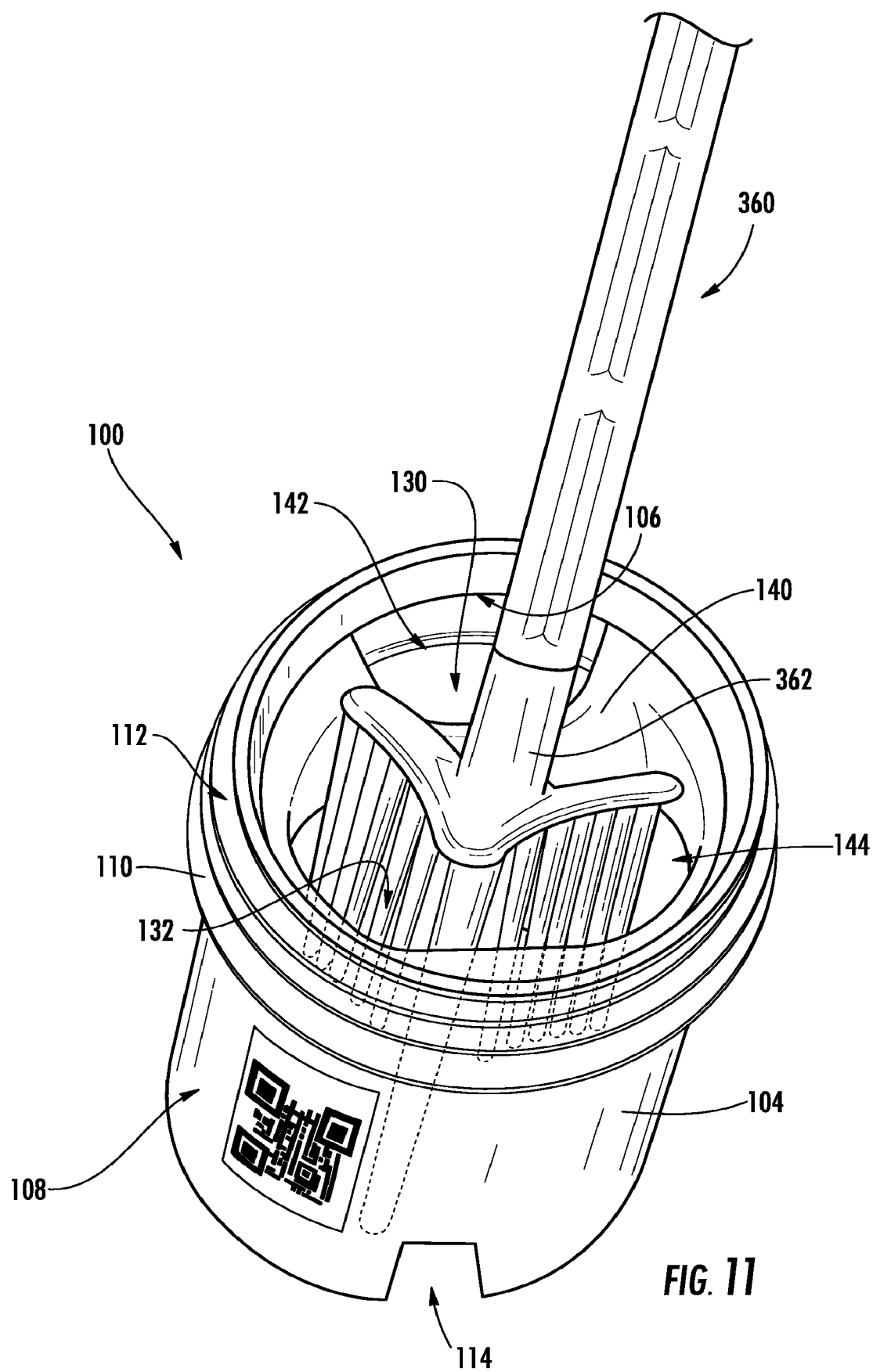

Having thus described the invention in general terms, reference will now be made to the accompanying drawings, which are not necessarily drawn to scale, and wherein:

FIG. 1 illustrates a specimen container assembly configured for collecting a biological specimen according to some embodiments of the present invention;

FIG. 2 illustrates a container configured for receiving and storing a biological specimen according to some embodiments of the present invention;

FIG. 3 illustrates a top view of the container shown in FIG. 2 according to some embodiments of the present invention;

FIG. 4 illustrates a container configured for receiving and storing a biological specimen according to some embodiments of the present invention;

FIG. 5 illustrates a top view of the container shown in FIG. 4 according to some embodiments of the present invention;

FIG. 6A illustrates a specimen container engaged with a sampling apparatus according to some embodiments of the present invention;

FIG. 6B illustrates a specimen container engaged with a sampling apparatus according to some embodiments of the present invention;

FIG. 6C illustrates a specimen container engaged with a sampling apparatus according to some embodiments of the present invention;

FIG. 7 illustrates a cap according to some embodiments of the present invention;

FIG. 8 illustrates a cap engaged with a chuck configured to disengage the cap from the specimen container according to some embodiments of the present invention;

FIG. 9 illustrates a sectional view of the cap engaged with a chuck shown in FIG. 8 according to some embodiments of the present invention;

FIG. 10 illustrates a sectional view of the specimen container assembly configured for collecting a biological specimen according to some embodiments of the present invention; and FIG. 11 illustrates a specimen container engaged with a specimen collection device according to some embodiments of the present invention.

DETAILED DESCRIPTION

Embodiments of the present invention will now be described more fully hereinafter with reference to the accompanying drawings, in which some, but not all embodiments of the invention are shown. Indeed, these embodiments may be embodied in many different forms and should not be construed as limited to the embodiments set forth herein; rather, these embodiments are provided so that this disclosure will satisfy applicable legal requirements Like numbers refer to like elements throughout. The terms top, bottom, side, up, down, upwards, downwards, vertical, horizontal, and the like, to the extent used herein, do not imply a required limitation in all embodiments of the present invention, but rather are used herein to help describe relative direction and/or orientation in the example embodiments illustrated in the figures.

Various embodiments of the present invention generally provide for an assembly for collecting, identifying, storing and preventing contamination of a biological sample, wherein the assembly generally includes a specimen container and a cap. For example, a specimen container may be configured to receive a biological sample therein from a specimen collection device, such as a brush or swab. Accordingly, embodiments of the present invention may facilitate the collection and/or storage of a biological sample within the container, such as a cytological sample obtained from the cervix and/or vagina with a specimen collection device. In addition, embodiments of the present invention may provide for the reduction in contamination of a biological specimen by providing a closed environment for storing the biological specimen. According to some embodiments, the container may be configured to provide accurate and efficient sample access, handling, and/or identification, such as during automated processes.

In this regard, FIG. 1 illustrates a specimen sample container assembly 10 that includes a container or vial 100 and a cap 200. According to one embodiment, the vial 100 and cap 200 may be configured to engage one another so as to collect, store, seal and/or preserve the specimen within the vial. Specifically, the cap 200 may be configured to be removably coupled to the vial 100 such that when the cap is coupled with the vial, the vial and cap create a closed and/or sealed environment preventing the contamination of a biological specimen stored therein. As such, FIG. 1 illustrates the specimen sample container assembly 10 according to one embodiment, wherein the vial 100 and cap 200 are secureably coupled to one another creating such a closed and/or sealed environment. In some embodiments, the vial 100 may include a base 102 and a perimeter wall 104, as shown in FIGS. 1 and 2. The perimeter wall 104 may extend vertically from the base 102 and define an interior surface 106 and an exterior surface 108. Although FIG. 2 illustrates an embodiment where the perimeter wall 104 may be cylindrical in shape, one of ordinary skill in the art may appreciate that the perimeter wall may include a variety of shapes.

FIG. 2 illustrates one embodiment of the present invention that includes a vial 100 having a flange 110 and a threaded surface 112 disposed on the exterior surface 108 defined by the perimeter wall 104 of the vial. According to one embodiment, the threaded surface 112 may be disposed vertically above the flange 110. The flange 110 and the threaded surface 112 may be configured to engage and secure the cap 200 to the vial 100. Although a threaded engagement between the vial 100 and cap 200 is described, it is understood that other engagement mechanisms may be employed, such as a snap, slotted, or twist-fit connection.

In some embodiments, the vial 100 may further include an alignment feature, such as a notch 114. According to some embodiments, the notch 114 may be defined, in part, by the perimeter wall 104 of the vial 100. In another embodiment, the notch 114 may be additionally defined, in part, by the base 102 of the vial 100. The notch 114 may be vertically disposed proximate to an end of the vial 100 opposite from the threaded surface 112 and/or flange 110. In some embodiments, the notch 114 may provide for orienting the vial 100 in subsequent automated processing, such as for loading the vial in a tray, accessing the contents of the vial and/or the like. For example, the notch 114 may be engaged by a corresponding engagement feature in a tray such that each vial 100 placed within the tray is oriented in a similar direction.

In some embodiments, the vial 100 may further include a tower 120 that extends upwardly from the base 102 of the vial, as shown in FIGS. 1 and 2. According to some embodiments, the tower 120 may be configured to partition the interior volume of the vial 100 into two separate chambers. Specifically, the tower 120 may partially define a first chamber 130 and a second chamber 132 within the vial 100, wherein the first and second chambers are in fluid communication with one another. According to some embodiments, the interior surface 106 of the perimeter wall 104 of the vial 100 may cooperate with the tower 120 to further define the first and second chambers 130, 132. Thus, the interior surface 106 and tower 120 may collectively define the first and second chambers 130, 132. In some embodiments, the first chamber 130 may be disposed approximately radially opposite from the notch 114. Accordingly, when the vial 100 is aligned in a particular orientation via the notch 114, the first chamber 130 will always be disposed in a known position such that access to the first chamber during, for example, aspiration or mixing of a biological specimen within the first chamber, will be efficient, repeatable and/or accurate. In some embodiments, the first chamber 130 may have a volume smaller than the volume of the second chamber 132. However, it is understood that the volumes of the first and second chambers 130, 132 could be the same or about the same, or the second chamber may have a smaller volume than the first chamber in some circumstances.

The tower 120 may include a top edge 122, as shown in FIG. 2. In some embodiments, the tower 120 may include at least one longitudinal edge 126. For example, the tower 120 may have a pair of longitudinal edges on opposite sides thereof, as shown in FIG. 3. In addition, the tower 120 may include a base edge 124 (see e.g., FIGS. 1 and 6A-6C). At least one longitudinal edge 126 may extend vertically upward from the base edge 124 of the tower 120. In some embodiments, the base edge 124 of the tower may be spaced apart from the interior surface 106 of the perimeter wall 104 such that the base edge does not contact the perimeter wall. Thus, the base edge 124 of the tower 120 may be formed or otherwise coupled to a base interior surface 134 of the vial 100 but not the interior surface 106. According to one embodiment, at least a portion of the longitudinal edge 126 may be spaced apart from the interior surface 106 of the perimeter wall 104 of the vial 100 so as to define at least one opening 118 between the first and second chambers 130, 132. FIG. 3 illustrates that an opening 118 may be defined along each longitudinal edge 126. As such, the at least one opening 118 provides for fluid communication between the first and second chambers 130, 132. In some embodiments, the entire length of the longitudinal edge 126 may be spaced apart from the interior surface 106 of the perimeter wall 104 such that the opening 118 also extends along the entire length of the longitudinal edge. Accordingly, the first chamber 130 and the second chamber 132 may be in fluid communication with one another along the entire length of the longitudinal edge 126.

Accordingly, a specimen collection device 360, such as a brush, may be placed within the second chamber 132 such that the vial 100 receives a biological specimen therein, as shown in FIG. 11. In some embodiments, the brush may include a detachable brush head 362 that may be configured to detach from the specimen collection device and remain within the second chamber 132 of the vial 100. According to one embodiment, the tower 120 may be configured to provide access for accessing the biological specimen via the first chamber 130 without contacting the detachable brush head of a specimen collection device disposed within the second chamber 132 of the vial 100.

According to another embodiment, the vial base 102 may define a base interior surface 134 that also defines the first and second chambers 130, 132. In some embodiments, the base interior surface 134 may be sloped and/or angled towards the tower 120 of the vial 100, as shown in FIG. 10. In some embodiments, the notch 114 may be disposed opposite from the tower 120, as shown in FIGS. 1-3 and 10. As such, the base interior surface 134 may define a downward slope such that the elevation of the base interior surface 134 disposed proximate to the notch 114 has a higher elevation than the base interior surface disposed proximate to the tower 120. Accordingly, the downward slope of the base interior surface 134 may provide for as much volume of a specimen to be aspirated from the vial 100, as gravity may assist in encouraging a greater quantity of the biological specimen to be disposed within the first chamber 130 of the vial.

FIG. 4 illustrates a vial 100 according to another embodiment of the present invention. The vial 100 includes an insert 140 disposed within the vial. According to some embodiments, the insert 140 may be integrally formed with the interior surface 106 of the peripheral wall 104 of the vial 100. In some embodiments, the insert 140 may be a separate component engaged or otherwise coupled to the interior surface 106. According to some embodiments, the insert 140 may be a separate component engaged or otherwise coupled with the tower 120. In some embodiments, the insert 140 may be integrally formed with the tower 120, as well as the interior surface 106 of the peripheral wall 104 of the vial 100. As discussed above, the tower 120 defines one or more openings 118 along the longitudinal edges. In one embodiment, an opening 118 is also defined between the base edge 124 of the tower 120 and the base interior surface 134. Thus, the tower 120 may not engage the base interior surface 134 when engaged with the insert 140.

In some embodiments, the insert 140 may define at least a first opening 142 and a second opening 144, as shown in FIGS. 4 and 5. According to some embodiments, the first opening 142 and second opening 144 are not in direct fluid communication with one another. Thus, the insert 140 may define separate openings 142, 144 that are only in fluid communication indirectly, such as via one or more openings 118 defined between the tower 120 and the interior surface 106 and base interior surface 134. Further, the first opening 142 may be configured to provide access to the first chamber 130, while the second opening 144 may be configured to provide access to the second chamber 132. In addition, the second opening 144 may be shaped such that a portion of the insert 140 extends between the second opening and the interior surface 106 of the peripheral wall 104 of the vial 100. As such, the second opening 144 may be configured to receive a specimen collection device, such as a brush, swab and/or the like, therethrough. In addition, in an instance where a specimen collection device 360 includes a detachable portion, such as a brush with a detachable brush head 362, the second opening 144 may be configured to assist in detaching the detachable portion of the specimen collection device such that the detachable portion of the specimen collection device remains within the second chamber 132, as shown in FIG. 11. Specifically, the portion of the insert 140 disposed between the second opening 144 and the interior surface 106 of the peripheral wall 104 may define an engagement surface that provides a resistive force to the detachable portion of the specimen collection device as the specimen collection device is being removed from the second chamber 132. For example, a brush 360 with a detachable brush head 362 may be inserted through the second opening 144 to provide the specimen sample to the vial 100. The brush may then be rotated and pulled upwardly so as to engage the insert 140 and detach the brush head within the vial 100.

As shown in FIGS. 6A-6C, the tower 120 may extend vertically to different heights within the vial 100. In this regard, the tower 120 may extend any desired distance between the base 102 and a top edge of the vial 100. For example, the tower 120 may extend vertically approximately three-quarters of the length of the vial 100, as illustrated in FIG. 6A. According to another embodiment, the tower 120 may extend vertically to approximately the length of the vial 100 from the vial base 102 proximate to the flange 110, such as to a horizontal plane that is co-planar with the flange 110 of the vial, as shown in FIGS. 6B and 6C. In addition, the tower 120 may be coupled and/or integrally formed with the insert 140, while extending from the vial base 102, as shown in FIG. 6B. FIG. 6C illustrates one embodiment where the tower 120 extends from the vial base 102 proximate to the flange 110, such as to a horizontal plane that is co-planar with the flange 110 of the vial 100 that does not include an insert 140. According to some embodiments, the tower 120 may extend vertically and parallel to a longitudinal axis of the perimeter wall 104. In addition, the tower 120 may include a generally C- or U-shaped cross section taken perpendicular to the longitudinal axis. However, the tower 120 may include different shapes and sizes depending on the particular specimen to be contained and accessed.

FIG. 7 illustrates a cap 200 configured to engage a vial (such as those described above) so as to create a sealed and/or closed environment for storing a biological specimen. Specifically, the cap 200 may include an interior surface 208, as shown in FIG. 9, configured to engage the outer surface 112 of the vial 100 so as to create a closed environment for storing the biological specimen. According to some embodiments, the interior surface of the cap 200 may include a reciprocal threaded interior surface configured to engage the threaded surface 112 of the vial 100. It is understood that the engagement may be accomplished using other mechanisms as discussed above, and the threaded engagement could be reversed if desired (i.e., the interior surface of the vial may be threaded and configured to engage a reciprocal cap surface, such as a threaded outer cap surface).

According to some embodiments, the cap 200 may include a pierceable surface 202. The pierceable surface 202 may include a portion of the cap 200 that includes a thinner dimension than other portions of the cap. For example, the pierceable surface 202 may be located generally in a central portion of the cap 200, although one or more pierceable surfaces could be defined to align with the first and/or second chambers 130, 132. As such, the pierceable surface 202 may be configured to be pierced by an instrument, such as a pipette, syringe, needle and/or the like. According to one embodiment of the present invention, the pierceable surface 202 may be pierced by an instrument such that a specimen may be aspirated from the vial 100 when the vial and cap 200 are sealingly engaged with one another. Accordingly, the contents of the container 10 may be accessed when the vial 100 and cap 200 are sealingly engaged with one another. In some embodiments, the pierceable surface 202 of the cap 200 may be pierced so as to allow for the introduction of a specimen into the container 10 when the vial 100 and cap are sealingly engaged with one another. In some embodiments, the pierceable surface 202 may be defined to align with the first chamber 130 such that an instrument, such as a syringe, may pierce the pierceable surface, mix the specimen sample, and/or aspirate at least a portion of the specimen without contacting a detachable portion of a specimen collection device, such as a detachable brush head, disposed within the second chamber 132 while the vial and cap are sealingly engaged with one another.

In some embodiments, the cap 200 may further include at least one finger 204 configured to be engaged by an engagement member, such as a chuck 250, as shown in FIG. 8. According to some embodiments, the cap 200 may include at least three fingers 204 equally spaced circumferentially around the cap. Specifically, the fingers 204 may be disposed at approximately 0, 120, and 240 degrees around the circumference of the cap 200. In some embodiments, the chuck 250 may include at least an equal number of chuck fingers 252 configured to engaged the fingers 204 of the cap 200 (e.g., one or more fingers 252). As such, the chuck fingers 252 may engage the fingers 204 so as to disengage the cap 200 from the vial 100. In some embodiments, the chuck fingers 252 may be configured to engage the fingers 204 of the cap 200 by rotating the chuck fingers in a direction opposite from each of the finger openings 206 defined by the respective fingers 204. As shown in FIG. 8, the chuck fingers 252 may rotate in a counter-clockwise direction to engage the fingers 204 of the cap 200, and may rotate in a clockwise direction to disengage the fingers of the cap. In some embodiments, the chuck 250 may be configured to temporarily disengage the cap 200 from the vial 100 while maintaining engagement of the cap, and subsequently re-engage the cap to the vial. According to some embodiments, the chuck 250 may be configured to disengage the cap 200 from the vial 100 in an automated process and re-engage the cap to the vial in another automated process. Specifically, the chuck 250 may be configured to disengage the cap 200 from the vial 100 to allow for a specimen to be placed, removed, processed and/or otherwise handled within the vial.

According to some embodiments, the container assembly 10 may further include indicia 370, such as a label, attached thereto, as shown in FIG. 2. For example, the indicia may include a visible identifier for identifying and/or facilitating chain of custody of the container assembly 10. Specifically, the indicia may include a tear-off portion with identifying information that corresponds to identifying information on the indicia remaining on the container assembly 10. In some embodiments, the indicia may include a barcode identifier or other identifier on both the portion of the indicia that remains disposed on the container assembly 10 and the tear-off portion of the indicia. Accordingly, the visual identifier, such as the barcode identifier, may assist in maintaining chain-of-custody controls while a specimen sample is tested via an automated processing machine and/or other manual processes. According to some embodiments, the tear-off portion of the indicia may be configured to affix to forms and/or documents to be used for processing and identification. As such, rather than generating labels in a processing center and affixing the labels to both the containers 10 and forms and/or other documents, the containers may be provided to the processing center with the indicia affixed thereto, thereby minimizing potential for mislabeling and other chain-of-custody issues. Although FIG. 2 illustrates the indicia 370 is shown to be affixed to the container 100, in some embodiments, the indicia may be affixed to a container cap 200. In another embodiment, the indicia may be affixed to both the container vial 100 and the container cap 200.

As such, embodiments of the present invention may provide a number of advantages, such as facilitating placement of a specimen and a specimen collection device within the specimen container. For example, according to some embodiments, the insert may facilitate placement of a detachable portion of the specimen collection device within one chamber while a tower disposed within the container allows for accessing the specimen in another chamber without disturbing and/or contacting the detachable portion of the specimen collection device. As such, some embodiments of the present invention may advantageously prevent cross-contamination of a specimen sample and/or may advantageously provide for the collection of the specimen sample without obstruction from a specimen collection device. Moreover, the tower may effectively delineate the container such that a portion of the sample is accessible (e.g., with a syringe) without interference from undesirable materials, such as mucous.

In some embodiments, the specimen container assembly may advantageously facilitate the placement of the specimen container within a sample tray configured to receive a number of specimen containers. According to some embodiments, an alignment feature, such as a notch, may be configured such that a specimen container including a notch may only be fully seated within a sample tray when the notch aligns with a reciprocal feature of the sample tray. Accordingly, the specimen container may be disposed correctly within a sample tray only when oriented in a particular fashion. As such, the specimen container may be positioned within the sample tray such that a first chamber for accessing the specimen stored within the container is positioned only at a particular location when the specimen container is fully seated within a sample tray. Thus, the specimen container assembly may advantageously provide a known path for aspirating and/or mixing a specimen sample with a syringe as the specimen container may only be disposed in a particular orientation.

Further, some embodiments of the present invention may advantageously provide for efficient capping and de-capping of a specimen container. For example, a container cap may include a plurality of fingers that are configured to engage an engagement member, such as a chuck, such that the container cap may be rotated and/or removed from the specimen container in an automated process. Some embodiments of the present invention may also provide for the engagement member to remain engaged with the container cap after the cap has been removed to facilitate the re-capping of the specimen container after a specimen sample has been aspirated. As such, some embodiments advantageously provide for a specimen container to be sealed with a cap previously engaged with the specimen container to prevent cross-contamination.

Many modifications and other embodiments of the invention set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for collecting a biological specimen, the method comprising:
 obtaining a biological specimen with a specimen collection device;
 inserting the specimen collection device into a container comprising:
  a peripheral wall extending from a base, wherein the peripheral wall and the base define an interior surface and an exterior surface, and wherein the peripheral wall of the container further comprises a flange and a threaded exterior surface disposed opposite from the base;
  a longitudinal tower disposed within the container, wherein the longitudinal tower forms a partition within the container to form at least a first chamber and a second chamber therein, wherein the first and second chambers are in fluid communication with one another; and
  an insert placed over and spanning the longitudinal tower, wherein the longitudinal tower defines a separation between a first portion of the insert over the first chamber and a second portion of the insert over the second chamber, wherein the first portion of the insert is not in fluid communication with the second portion of the insert, and wherein the specimen collection device is received by the second chamber; and
 sealing the interior surface of the container with a cap, wherein the cap comprises a pierceable portion located above the first chamber and plurality of fingers that are configured to engage a chuck, wherein the step of sealing the interior surface of the container includes engaging the cap with the flange and the threaded exterior surface of the peripheral wall of the container and wherein the step of sealing the interior surface of the container further includes engaging the fingers of the cap with an equal number of fingers of a chuck and rotating the chuck in a clockwise or counter-clockwise direction.

2. The method of claim 1 further comprising:
leaving a portion of the specimen collection device within the second chamber when the remainder of the specimen collection device is removed from the container;
inserting at least a portion of a syringe into the first chamber of the container; and
using the syringe to remove at least a portion of the biological specimen from the container.

3. The method of claim 1 further comprising:
engaging the second chamber of the container and the second portion of the insert of the container with the specimen collection device to thereby leave a portion of the specimen collection device within the second chamber of the container.

4. The method of claim 3 further comprising:
piercing, with an instrument, the pierceable portion of the cap; and
aspirating, with the instrument, a portion of the biological specimen from the first chamber of the container without contacting the portion of the specimen collection device left within the second chamber of the container.

5. The method of claim 3, wherein the specimen collection device is a brush and the portion of the specimen collection device left within the second chamber of the container is a detachable brush head.

6. The method of claim 5, wherein the step of engaging the second chamber of the container and the second portion of the insert of the container with the brush includes rotating the brush and pulling upwardly on the brush to thereby leave the detachable brush head within the second chamber of the container.

7. The method of claim 3 further comprising:
aspirating, with an instrument, a portion of the biological specimen from the first chamber of the container without contacting the portion of the specimen collection device left within the second chamber of the container.

8. The method of claim 7, wherein the instrument is at least one of a pipette, a syringe, or a needle.

9. A method for collecting a biological specimen, the method comprising:
obtaining a biological specimen with a specimen collection device; and
inserting the specimen collection device into a container comprising:
a peripheral wall extending from a base, the peripheral wall and base defining an interior surface and an exterior surface;
a longitudinal tower disposed within the container, wherein the longitudinal tower forms a partition within the container to form at least a first chamber and a second chamber therein wherein the first and second chambers are in fluid communication with one another;
an insert placed over and spanning the longitudinal tower, wherein the longitudinal tower defines a separation between a first portion of the insert over the first chamber and a second portion of the insert over the second chamber, wherein the first portion of the insert is not in fluid communication with the second portion of the insert, and wherein the specimen collection device is received by the second chamber; and
a notch defined in the exterior surface and configured to position the container in subsequent processing wherein the longitudinal tower of the container is disposed within the container such that the first chamber is located approximately radially opposite from the notch, and wherein the base of the container is sloped downwards from the notch towards the longitudinal tower.

10. The method of claim 9, wherein a volume of the first chamber of the container is less than a volume of the second chamber of the container.

11. The method of claim 9, wherein the longitudinal tower of the container further comprises a base edge adjacent to the base and at least two longitudinal edges extending therefrom and are spaced apart from the peripheral wall, wherein the base edge and the at least two longitudinal edges do not contact the interior surface of the peripheral wall.

12. The method of claim 9, wherein the first portion of the insert of the container is an opening configured to provide access to the first chamber of the container, and wherein the second portion of the insert of the container is an opening configured to provide access to the second chamber of the container.

13. The method of claim 9, wherein the first portion of the insert of the container is configured to receive at least one of a pipette, a syringe, or a needle for aspirating a portion of the biological specimen from the first chamber of the container.

14. The method of claim 13, wherein the second portion of the insert of the container is configured to engage a specimen collection device to thereby leave a portion of the specimen collection device within the second chamber of the container.

15. A method for collecting a biological specimen, the method comprising:
obtaining a biological specimen with a specimen collection device; and
inserting the specimen collection device into a container comprising:
a peripheral wall extending from a base, the peripheral wall and base defining an interior surface and an exterior surface;
a longitudinal tower disposed within the container wherein the longitudinal tower forms a partition within the container to form at least a first chamber and a second chamber therein, wherein the first and second chambers are in fluid communication with one another, and wherein the longitudinal tower of the container further comprises a base edge adjacent to the base and at least two longitudinal edges extending therefrom and are spaced apart from the peripheral wall, wherein the base edge and the at least two longitudinal edges do not contact the interior surface of the peripheral wall; and
an insert placed over and spanning the longitudinal tower, wherein the longitudinal tower defines a separation between a first portion of the insert over the first chamber and a second portion of the insert over the second chamber, wherein the first portion of the insert is not in fluid communication with the second portion of the insert and wherein the specimen collection device is received by the second chamber.

16. The method of claim 15, wherein a volume of the first chamber of the container is less than a volume of the second chamber of the container.

17. The method of claim 15, wherein the longitudinal tower of the container extends parallel to a longitudinal axis of the peripheral wall of the container.

18. The method of claim 15, wherein the first portion of the insert of the container is an opening configured to provide access to the first chamber of the container, and wherein the second portion of the insert of the container is an opening configured to provide access to the second chamber of the container.

19. The method of claim 15, wherein the first portion of the insert of the container is configured to receive at least one of a pipette, a syringe, or a needle for aspirating a portion of the biological specimen from the first chamber of the container.

20. The method of claim 19, wherein the second portion of the insert of the container is configured to engage a specimen collection device to thereby leave a portion of the specimen collection device within the second chamber of the container.

* * * * *